United States Patent [19]

Kobayashi et al.

[11] Patent Number: 4,479,797
[45] Date of Patent: Oct. 30, 1984

[54] MEDICATION INFUSION DEVICE

[75] Inventors: Susumu Kobayashi; Yasuaki Shimojo, both of Fujinomiya, Japan

[73] Assignee: Terumo Corporation, Tokyo, Japan

[21] Appl. No.: 388,919

[22] Filed: Jun. 16, 1982

[30] Foreign Application Priority Data

Jul. 4, 1981 [JP] Japan .................. 56-104819

[51] Int. Cl.³ ............................................. A61M 5/00
[52] U.S. Cl. .................... 604/153; 417/474; 417/510
[58] Field of Search .............. 604/151–153, 604/65–67; 417/474, 478, 479, 510

[56] References Cited

U.S. PATENT DOCUMENTS

| 2,105,200 | 1/1938 | Phelps | 417/474 |
| 2,625,932 | 1/1953 | Salisbury | 604/153 X |
| 3,658,445 | 4/1972 | Pulman et al. | 417/474 |
| 3,679,331 | 7/1972 | Kushner | 417/478 |
| 3,778,195 | 12/1973 | Bamberg | 417/474 |
| 4,236,880 | 12/1980 | Archibald | 417/478 |
| 4,273,121 | 6/1981 | Jassawalla | 604/153 |

FOREIGN PATENT DOCUMENTS

2000833 1/1979 United Kingdom .
2016608 9/1979 United Kingdom .

Primary Examiner—Dalton L. Truluck
Attorney, Agent, or Firm—Frishauf, Holtz, Goodman and Woodward

[57] ABSTRACT

A liquid medication infusion device includes a number of elongate fingers each displaceable in a predetermined sequence by associated cams driven by drive means such as a motor. A feeding tube for liquid medication, when placed between said fingers and a cap, is squeezed by the fingers to infuse liquid medication into a human body. The fingers comprise at least three fingers arranged parallel to one another with a central finger and side fingers arranged on either side of the central finger. The central and side fingers are formed integrally with a support member and are each carried at first ends by the support member in cantilevered fashion. The side fingers are shaped for squeezing the feeding tube at corresponding substantially point locations on the tube to completely collapse the tube, and the central finger is shaped for squeezing the feeding tube over a required length between the point locations for pumping the medication in the tube. Each finger has its cantilevered end portion reduced in thickness for providing a spring action.

9 Claims, 17 Drawing Figures

MEDICATION INFUSION DEVICE

BACKGROUND OF THE INVENTION

This invention relates to a medication infusion device having a finger type pump unit wherein three or more fingers are moved in a predetermined sequence, and wherein a feeding tube for medication is placed between a cap and said fingers, and squeezed by said fingers to infuse the medication into the human body.

An infusion device of the type described has been proposed for infusion of a small amount of medication such as insulin. For example, in the treatment of a diabetic patient, it is necessary that insulin be continuously and cyclically infused into the body of the patient. Since the insulin requirement of a patient is subject to substantial fluctuations caused by the meal cycle, sleep or energy consumption as when the patient walks, a small-sized portable insulin infusion device has been proposed in which prescribed infusion doses are preset for certain times so that cyclic insulin infusion may be made in accordance with the insulin requirements of the body that change with time. The infusion device defined above may be applied to the proposed insulin infusion device.

The insulin infusion device has a memory in which the amount of liquid infused per unit time may be programmed on the basis of the presumed physical condition and behavior of the patient over a twenty-four hour period. The device also has a clock generator for generating clock pulsed for calling data from memory at predetermined time intervals, and a motor drive circuit for rotating a motor a certain number of revolutions conforming to the data called forth from the memory by the clock. The pump unit and the pump control unit may be enclosed in respective casings. The pump unit acts to dispense the liquid by squeezing or collapsing the feeding tube of a disposable insulin vessel and may operate for a required time interval such as one minute, as instructed by the pump control unit for dispensing the required insulin dose programmed in the memory.

The infusion device of this kind may be applied not only to the infusion of insulin but also to any repeated and continued infusion treatment in which liquid medication is administered in equal or differing doses per time unit.

The prior-art pump does not lend itself to a reduction in size easily because of the large number of components and numerous assembly steps. Moreover, a small-sized pump exhibits disminished durability, while the amount of dispensed liquid cannot be adjusted minutely without considerable difficulties. Thus it is not easy to obtain an infusion device by using a small sized version of the prior-art pump.

Figure 1:
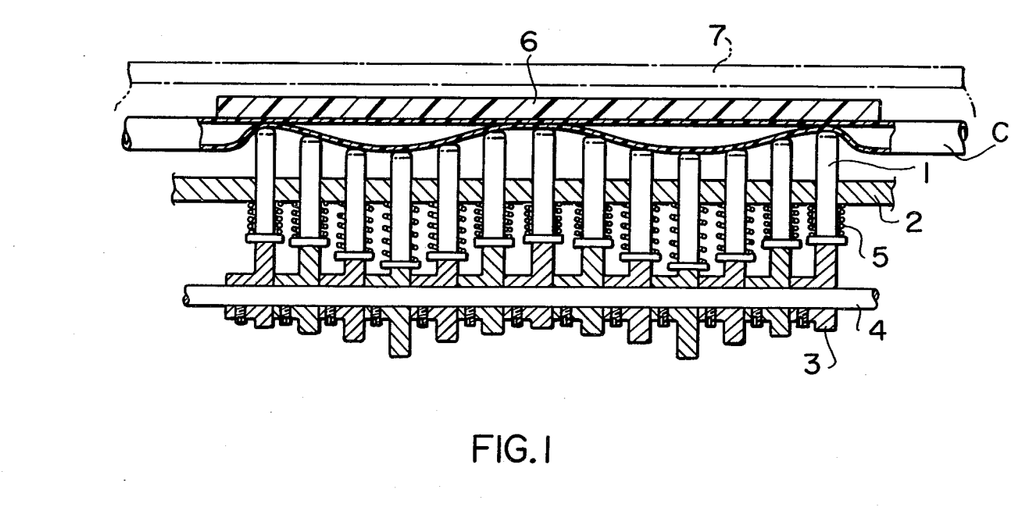
FIG. 1 is a sectional view showing an essential part of the prior-art finger-type compact pump unit for infusion of liquid medication.

FIG. 1 shows a prior-art finger type pump unit including a feeding tube C, fingers 1, finger guides 2, cams 3, a cam shaft 4, coil springs 5, a cap 6 and a casing 7. Liquid may be dispensed by sequential actuation, in the liquid feed direction, of the fingers which are capable of squeezing the tube C. At least three fingers 1 are required in this case, but a larger number of fingers 1 are required to dispense the liquid smoothly. The number of cams 3 and coil springs 5 required is the same as the number of the fingers 1. A large number of components and manufacturing steps are required and space must be provided for housing and assembly of these components, thus making it difficult to reduce the size of the pump unit and infusion divice. Furthermore, adjustment of the amount of liquid dispensed per revolution of the cam shaft of the finger-type pump unit is practically impossible due to structural limitation. Also, loss of electrical power due to friction between a multiplicity of fingers and finger guides cannot be neglected in view of the limited power supply of the portable type infusion device.

SUMMARY OF THE INVENTION

The present invention has been devised with the foregoing in view and has as its object to provide a medication infusion device having a finger-type pump unit which is small in size and light in weight and durable in construction, and which has a markedly reduced number of components such as finger guides, and fewer manufacturing steps.

According to the present invention, the foregoing and other objects are attained by providing a medication infusion device of the type having a finger-type pump unit, the pump unit having a cap and three or more fingers displaceable towards the cap in a predetermined sequence by operation of cam means driven by rotary drive means, the fingers being operative to squeeze a feeding tube for infusion of liquid medication when the feeding tube is located between the cap and the fingers, wherein the improvement resides in that said three or more fingers comprise two side fingers placed in side-by-side relation with at least one inner or central finger, the side fingers being capable of squeezing or completely collapsing the feeding tube at substantially one point, and the central finger being capable of squeezing the feeding tube over a required length for pumping medication in the tube, the fingers being carried by a support member at first ends of the fingers, and a plurality of cams each having a specific cam profile and being operatively associated with each finger for operating said finger, the cams having a common axis in the transverse direction of the fingers.

In short, the side fingers of the finger-type pump unit are reduced in tube contact width so as to provide a fluid valve function, the central finger is increased in width so as to provide a pumping function, the fingers are supported by a support member in cantilever fashion, and the cams are formed as one piece having a common axis.

It is a further object of the present invention to provide a medication infusion device which is small in size, reliable in pumping performance and adjustable in terms of dispensed dose, and which features improved fabrication and assembly accuracy for the fingers, cams, support frame or motor base and which may be manufactured at reduced cost.

In accordance with the present invention such further object may be attained by an improved medication infusion device in which the support member and the fingers of the finger-type pump unit are molded or machined integrally from a resilient plastic material, and the fingers are reduced in thickness in the direction of the cap and cams at the cantilevered ends so as to form leaf spring portions, or by an alternative arrangement in which the support member and the fingers of the finger-type pump unit are molded or machined integrally from a crystalline plastic material such as polyacetal, polyethylene, polyamide or polypropylene and the fingers are reduced in thickness at the cantilevered ends substantially along a line extending in the sidewise direction of the fingers so as to form folding portions. Such further object may be attained by still another arrangement in which the support member for mounting the fingers, the cap and the cams are formed as a support frame encircling the fingers in substantially the same plane as the fingers, and in which the upper half frame portions of the support frame on both sides of the side fingers are provided with slits on surfaces thereof facing the cap, the slits being aligned in the sidewise direction of the fingers and accommodating the feeding tube in a stable state. As a further alternative, a flexible gap control sheet or plate may be placed directly on the surface of the cap facing the central finger, while the sheet or plate may be secured to the cap at an end opposite to its abutment portion with the feeding tube, but not secured at the other end, so that the abutment portion may be urged from the cap by an adjustment screw threadedly mounted on the cap. In yet another arrangement, a mounting plate for mounting rotary means such as a motor may be formed integrally with a support frame, and the mounting plate may be provided with slits so as to render the mounting plate flexible relative to the support frame. Still alternatively, the cams may be formed as one piece having a common axis, with the end cam portions having a maximum radius less than the minimum radius of the axially central cam portion adjacent to the end cam portion.

BRIEF DESCRIPTION OF THE DRAWINGS

FIGS. 2 to 15 illustrate a compact portable liquid medication infusion device having a finger-type compact pump unit for infusion of liquid medication according to various embodiments of the present invention, in which

DESCRIPTION OF THE PREFERRED EMBODIMENT

Figure 2:
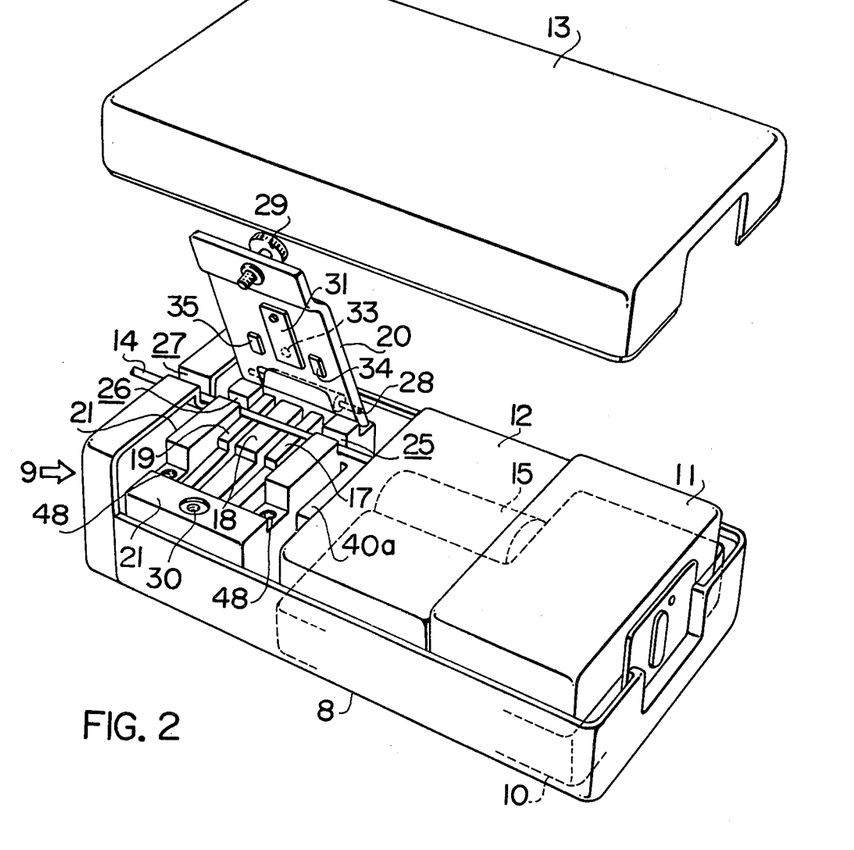
FIG. 2 is a perspective view of the overall device with a cover case removed to show the internal structure.
Figure 3:
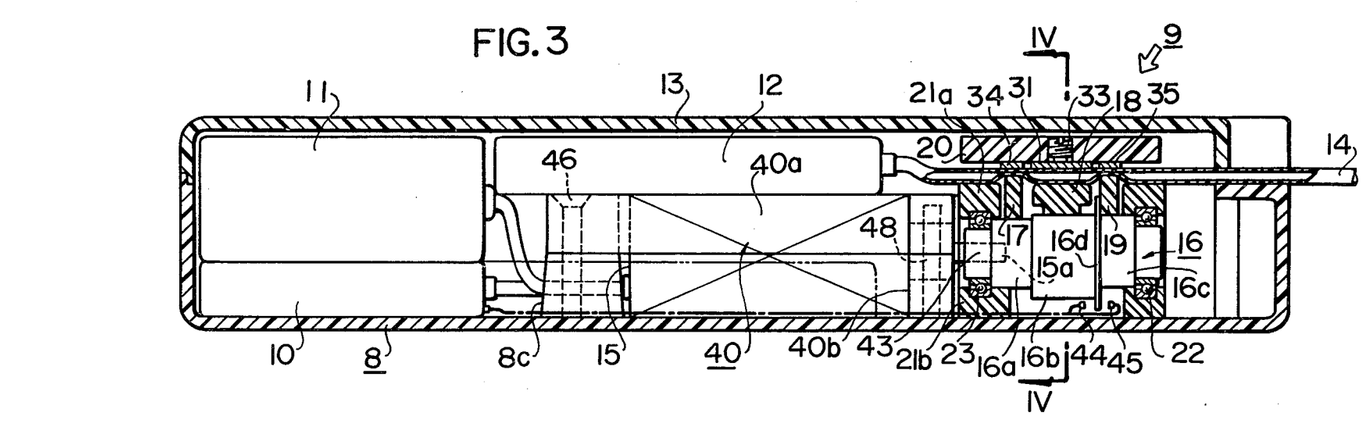
FIG. 3 is an enlarged longitudinal section of the casing of the device in FIG. 2.
Figure 4:
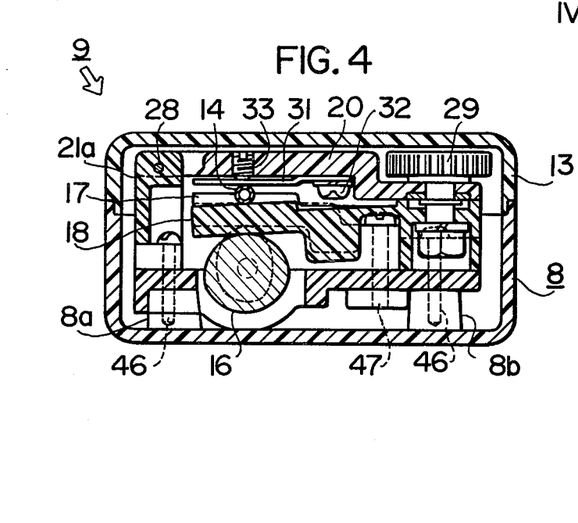
FIG. 4 is a sectional view taken along line IV—IV of FIG. 3.
Figure 5:
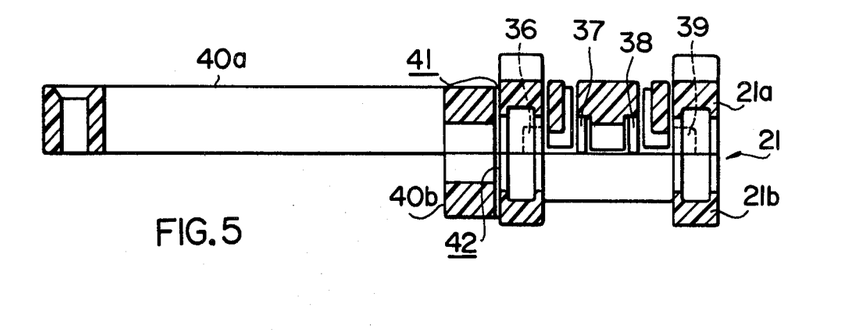
FIG. 5 is a sectional view showing the support frame divided or split into upper and lower half sections.

FIGS. 2, 3 and 4 show a small-sized portable medication infusion device suitably employed as an insulin injection device. The device includes a casing 8 enclosing a pump unit 9, a pump control unit 10, a battery 11 and a disposable medication bag 12, and may be hermetically sealed by a cover 13. The device is so constructed that, upon activation of a switch (not shown) to turn on the battery 11, different commands stored in memory are sent to the pump control unit 10 at predetermined time intervals so that the pump 9 operates to squeeze or collapse a feeding tube 14 repeatedly, to dispense the medication from the medication bag into a catheter (not shown) inserted into the human body.

The present invention is directed to a medication infusion device having the pump unit 9 controlled by any of a variety of control means including on/off switching devices for the power source, or automatic control means aided by microcomputers.

Referring now to the pump unit 9, the unit 9 preferably is contained in a casing along with the pump control unit 10, but these components may also be contained in separate vessels. The pump unit 9 need not be constructed to enclose the disposable medication bag 12, it being only necessary that the feeding tube 14 be sandwiched and collapsed or squeezed to effect infusion of the liquid medication.

Figure 6:
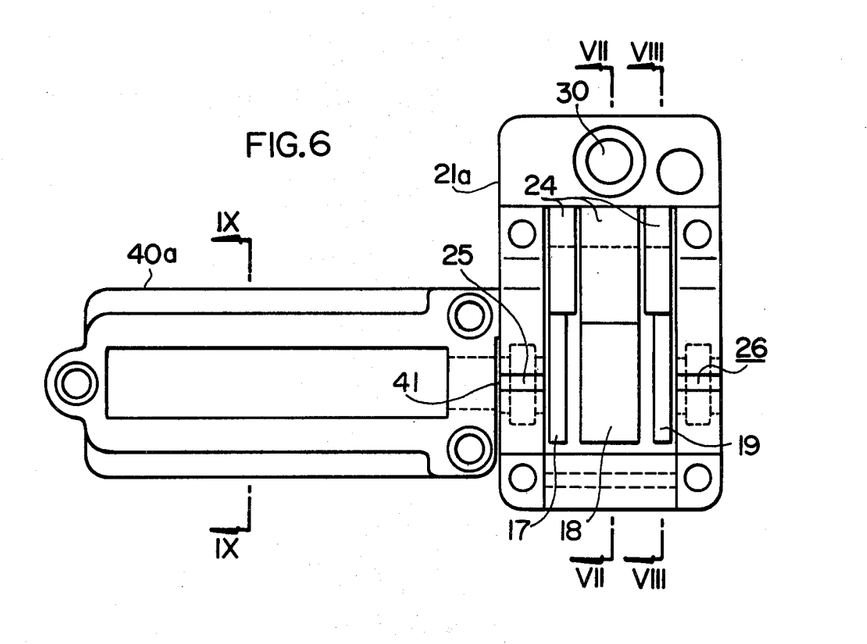
FIG. 6 is a plan view of the upper half frame section.
Figure 7:
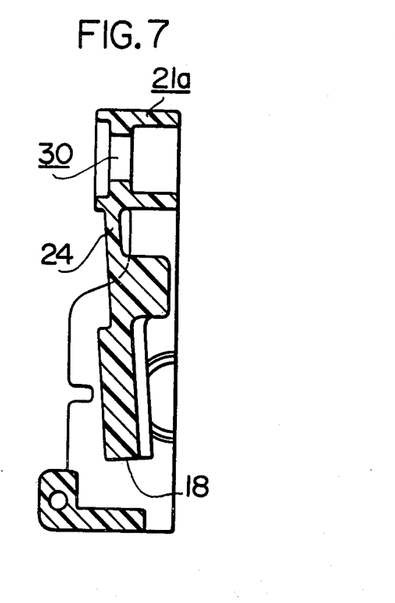
FIGS. 7, 8 and 9 are sectional views taken along lines VII—VII, VIII—VIII and IX—IX of FIG. 6.
Figure 8:
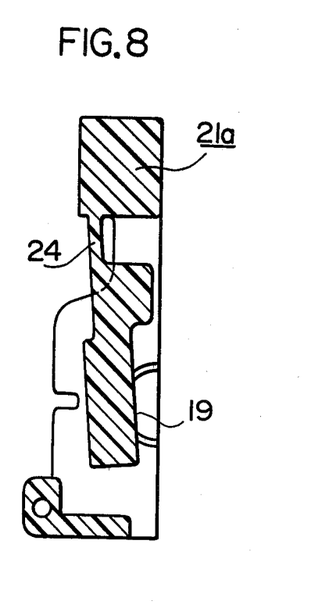
Figure 9:
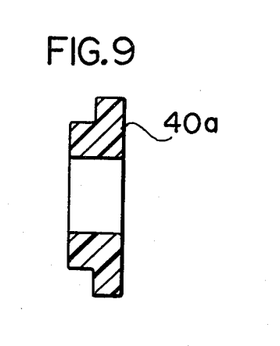
Figure 10:
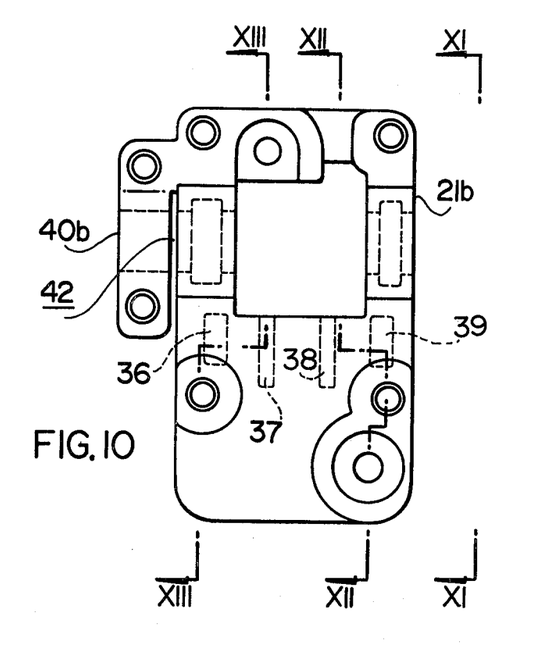
FIG. 10 is a bottom view of the lower support frame section.
Figure 11:
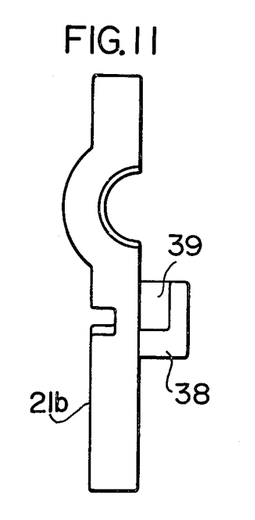
FIGS. 11, 12 and 13 are sectional views taken along lines XI—XI, XII—XII and XIII—XIII of FIG. 9.
Figure 12:
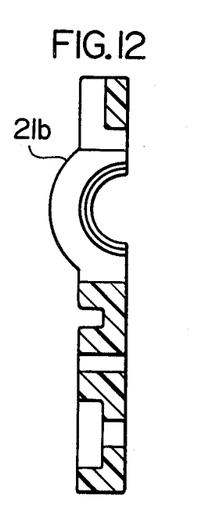
Figure 13:
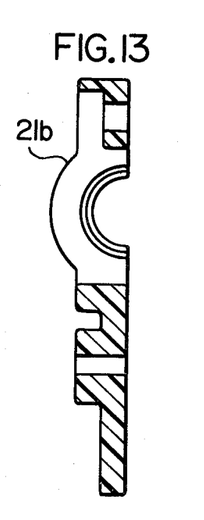
Figure 14:
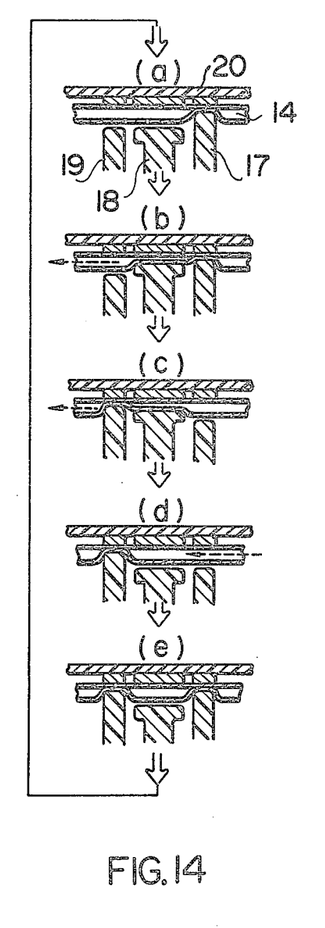
FIGS. 14 and 15 show different sequential steps in finger operation for describing the peristaltic finger movement of three fingers.
Figure 15:
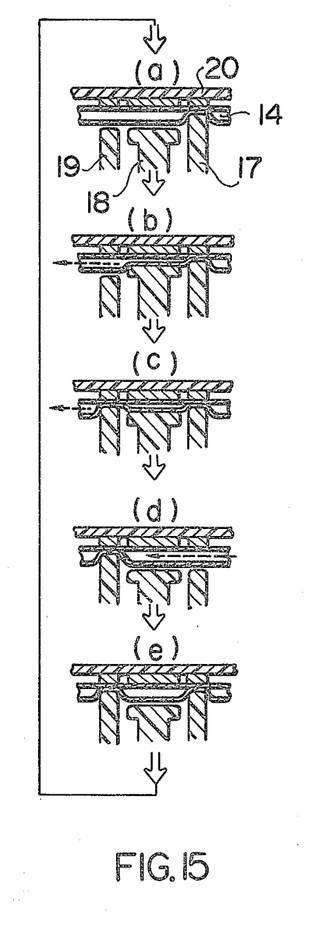

The pump unit 9 must have rotary drive means 15 such as a motor. An arrangement will suffice in which the feeding tube 14 of the medication bag 12 is placed between a cap 20 and fingers that are peristaltically moved by operation of a cam 16 driven in turn by the rotary drive means 15. The feeding tube 14 is squeezed by the fingers to effect liquid infusion. The three fingers 17, 18, 19 are placed side-by-side and the side fingers 17, 19 are of lesser width than the central finger, so that the feeding tube 14 may be collapsed substantially by point engagement to reduce the force required to completely collapse the tube and, hence, to lighten the burden of the drive system. The inner or central finger 18 is of larger width so as to have a pumping capability to collapse the tube 14 over a required length, in order to afford an effective peristaltic liquid feeding function with the use of a minimum number of fingers so as to reduce the number of components and manufacturing steps. The fingers 17, 18, 19 are surrounded by a box-shaped support frame 21 on which the fingers 17, 18, 19, the cap 20 and the cam 16 are mounted. As shown in FIGS. 5 to 13, the support frame 21 is divided into upper frame sections 21a facing the fingers, and lower frame sections 21b facing the lower surface of a cam 16, and is adapted to hold the cam 16 on either side by bearings 22, 23. These bearings are used to prevent power loss in the drive system. The cam 16 is formed as one piece with a common axis. The cam 16 has end cam portions 16a, 16c of maximum radii which are smaller than the minimum radius of the axially central cam portion 16b, as shown in FIG. 3. With such a cam profile, the cam can be extracted from the mold in the axial direction when molded as one piece to reduce assembly error, so that loss of motive power due to friction with the fingers, caused by burrs or like irregularities on the cam surface, may be prevented. As shown in FIGS. 6, 7 and 8, the upper frame sections 21a are formed integrally with fingers 17, 18, 19, and the cantilevered end portions of the fingers 17, 18, 19 are reduced in thickness in the direction of the cap and cam and are arranged as plate spring portions 24. The purpose of such structure is to enhance machining and assembly precision through integral molding, and to free the fingers for the purpose of reducing power loss caused by friction with finger guides. Longitudinally extending slits 25, 26 facing the cap 20 are provided in the faces of the frame portion adjacent to the fingers 17, 19, while a slit 27 is provided in the upper surface of the casing 8 facing the pump unit 9. The purpose of such structure is to stabilize the disposable medication bag 12 by being linearly positioned in the slits 25, 26, 27. As shown in FIGS. 2 and 4, the cap 20 is pivotally mounted by a pin shaft 28 to one side of the support frame section 21a. The cap has a screw 29 which may be engaged with or disengaged from a tapped hole 30 in the frame portion 21a towards the finger root for opening or closing the cap. A flexible metal or plastic sheet 31 is mounted on the surface of the cap 20 facing the fingers, so as to be intimately contactable with the central finger 18, and is secured to cap 20 with a screw 32 or an adhesive at an end portion of the sheet 31 free from contact with the feeding tube 14. An adjustment screw 33 operative from the cap side of the sheet 31 is threadedly mounted through sheet 31 at the position contactable with feeding tube 14. The purpose of such structure is to adjust the gap by adjustment of the screw 33 and, hence, to adjust the extent to which the feeding tube 14 is squeezed, thereby regulatng the flow of liquid medication. The preferred degree of adjustment is such as will not completely collapse the feeding tube 14, in order to provide smooth and durable restoration of the tube 14. Rubber segments 34, 35 are mounted on the same surface of the cap 20 and at positions registering with the side fingers 17, 19 and abuttable on the feeding tube 14, in order to provide smooth and durable tube restoration and to prevent the fracture of the feeding tube 14 if the feeding tube is crushed completely by the side fingers 17, 19 over a number of times. The minimum gap between the rubber segments and the side fingers is selected to be considerably less than twice the standard tube thickness to allow for compression of the rubber segments to a corresponding amount so that the tube can be squeezed fully in spite of fluctuations in tube thickness. The lesser the tube thickness, the lesser the amount of compression of the rubber plate. The cam 16 is formed integrally with end cam portions 16a, 16c slidably engaged with side fingers 17, 19, central cam portion 16b slidably engaged with central finger 18 and a sensing plate 16d having equiangular peripheral slits for sensing the number of motor revolutions. Adopting such an integral molding operation is useful in reducing the number of components and manufacturing steps and in increasing productivity and assembly accuracy. Cam portions 16a, 16b, 16c have different cam profiles of the desired shape, e,g. eccentric circles. Since the cam portion 16b has a minimum radius which is more than the maximum radius of the cam portions 16a, 16c, it is possible to extract the metallic mold axially of the cam so that the cam can be molded integrally without forming burrs on the cam surface, so that there is little loss of driving power. The correlation of these cam profiles are selected so that the fingers 17 to 19 may be peristaltically displaced as shown in FIG. 14 or 15 for the tube squeezing process. The cam 16, fingers 17, 18, 19 and the support frame 21 are molded from highly wear-resistant plastic materials such as polyacetal, polyamide, polyethylene, polypropylene or fluorine resin, in order to prevent wear due to sliding contact between the cam 16 and the fingers 17, 18, 19 and to assure a long-lasting pumping function. The fingers 17, 18, 19 are placed side-by-side in order to minimize the pump unit size and to assure an efficient pumping function by eliminating gaps which are excessively wide. Each leaf spring portion 24 of the thin-walled finger root has a rectangular cross-section. The lower frame portion 21b has finger guides 36, 37, 38, 39 adapted to enter the gaps on both sides and between the fingers 17, 18, 19 in order to prevent the fingers 17, 18, 19 from interfering with each other due to flexure of the fingers caused by the cam portions 16a, 16b, 16c.

The finger guides of the present invention are not ordinarily in contact with the fingers, unlike the guides used in the conventional device, and may be used advantageously with a battery-driven injection device because no loss of driving power results from frictional contact with the guide during the finger operation.

The rotary drive means 15 is a miniature coreless motor fitted with a reduction gear and clamped in position by an upper mounting plate 40a and a lower mounting plate 40b to facilitate the assembly operation. The upper mounting plate 40a is formed integrally with the upper frame sections 21a while the lower mounting plate 40b is formed integrally with the lower frame sections 21b. The purpose of such integral molding is to reduce the number of components, to enable the components to be manufactured with great accuracy and uniformity and to maintain assembly precision. Elongate slits 41, 42 are provided respectively in the connecting portion between the plate 40a and frame sections 21a and in the connecting portion between the plate 40a and frame sections 21b for absorbing looseness or mounting error between the motor 15 and mounting plates 40a, 40b, and for assuring smooth motor operation. The coreless motor 15 has an output shaft 15a which projection into an axial bore in the cam 16 and is connected thereto by a pin 43. A light emitter 44 and a light receiver 45 are mounted on both sides of and in opposition to the peripheral slits in the sensing plate 16d of the cam 16 for supplying the pump control unit 10 with feedback signals indicative of the number of revolutions of the cam 16.

In mounting the pump unit 9 in the casing 8, the cam 16 is fit on the lower frame sections 21b along with the bearings 22, 23 disposed on either side of the cam 16. With the neck of the output shaft 15a of the motor 15 placed on the lower mounting plate 40b, the output shaft 15a is inserted into the axial bore 16e of the cam 16, and the pin 43 is driven in place for connecting the cam 16 to the motor 15. Then, the upper frame sections 21a are placed on the lower frame sections 21b and connected thereto by a screw 47. The upper mounting plate 40a is secured in place by a screw 48. The support frame 21 is placed on base blocks 8a, 8b provided on the bottom surface of the casing 8 and is secured thereto by a screw 46. The cap 20 with built-in gap adjustment sheet 31, adjustment screw 33, screw 29 and rubber segments 34, 35 is pivotally mounted by pin shaft 28 on the upper frame portion 21a. According to the present invention, adjustment of the cam 16 and fingers 17, 18, 19 is unnecessary.

The operation of the pump unit 9 will now be described in connection with the medication infusion device of the present invention. In using the device, a disposable bag 12 is placed in the casing, the cap 20 is opened, the feeding tube 14 is layed in the slits 25, 26, 27 and on the fingers 17, 18, 19, and the casing cover 13 is closed. Then, as the power source is turned on, control unit 10 is driven into operation by power supplied by the battery. The control unit 10 has a memory, a clock for calling data from the memory, and a motor driving circuit designed to rotate the motor a certain number of revolutions commensurate with the data obtained from the memory. The clock is active at all times and calls the specified memory locations after the lapse of a predetermined unit time such as one minute. The memory stores a program defining the infusion dose per minute determined beforehand and based upon the patient's meal time, ambulation and sleep or rest periods. Thus the memory issues the specified signal called by the clock. The motor drive circuit converts the signal into a form indicative of motor revolution and delivers the converted signal at one-minute intervals for driving the motor 15 of the pump unit 9 accordingly. In the present embodiment, the memory locations addressed are changed at intervals of 15 minutes. The pump unit 9 then operates to squeeze the tube 14 repeatedly to dispense the medication in the bag 12 into the catheter inserted into the patient's body.

In operation of the pump unit 9, when the motor 15 is driven into rotation, the cam 16 is rotated very slowly by operation of a reduction gear so that the fingers 17, 18, 19 are peristaltically displaced by the cam portions 16a, 16b, 16c, as shown in FIG. 14 or 15 to repeatedly squeeze the feeding tube 14 between them and the cap 20. Thus, upon each squeezing action of the central finger 18, liquid medication is fed into the catheter in an amount corresponding to the squeezed tube volume.

The medication infusion device of the present invention having the finger-type pump unit is not limited to the above embodiment of the invention, but may be modified in a number of ways. Specifically, the finger-type pump unit to be employed in the present invention may be subjected to the following modifications:

(a) The rotary drive means 15 is not limited to an electrical motor but may comprise other drive means such as a hand-wound clock. When the pump unit 9 is used for infusion of insulin, the use of an electric motor calls for the installation of speed reducing means because of the extremely small infusion doses involved.

(b) More than one central finger 18 can be used. The central finger 18 may have any specific width depending on the amount of liquid dispensed and the rotational speed as well as the number of revolutions of the motor 15. Rather than having a single central finger of a large width, however, the finger may be divided into two or three portions, and the number of cam discs on the cam 15 may be increased correspondingly for peristaltic operation of the fingers.

(c) The cap 20 need not be designed to open pivotally as in the manner of a door, but may be fastened at four locations by means of screws.

(d) Two or more central fingers 18 may be provided instead of one. In such case, the number of cam portions must be increased correspondingly. In using, for instance, five fingers, the fingers must be moved by a sequence as shown in the finger process diagram of FIG. 16 by suitable selection of the operative relation between the fingers and the cam portions.

(e) The slits 25, 26 for accommodating the feeding tube 14 stably in the support frame 21 are not always necessary. For example, in the embodiment shown in FIG. 2, the slits 25, 26 may be omitted when the slit 27 in the casing 8 is sufficient to hold the tube 14 in stable fashion. Alternatively, suitable engaging means may be provided in the casing 8 separately from the support frame 21, or on both sides of the casing when only the pump unit 9 is contained in the casing.

(f) The fingers and the support frame need not be molded but may be machined into a unitary body.

(g) The mounting plate 40 for the motor may be provided separately from the support frame 21.

(h) The sensing plate 16d may be separately provided and assembled on the cam 16.

Figures 16, 17:
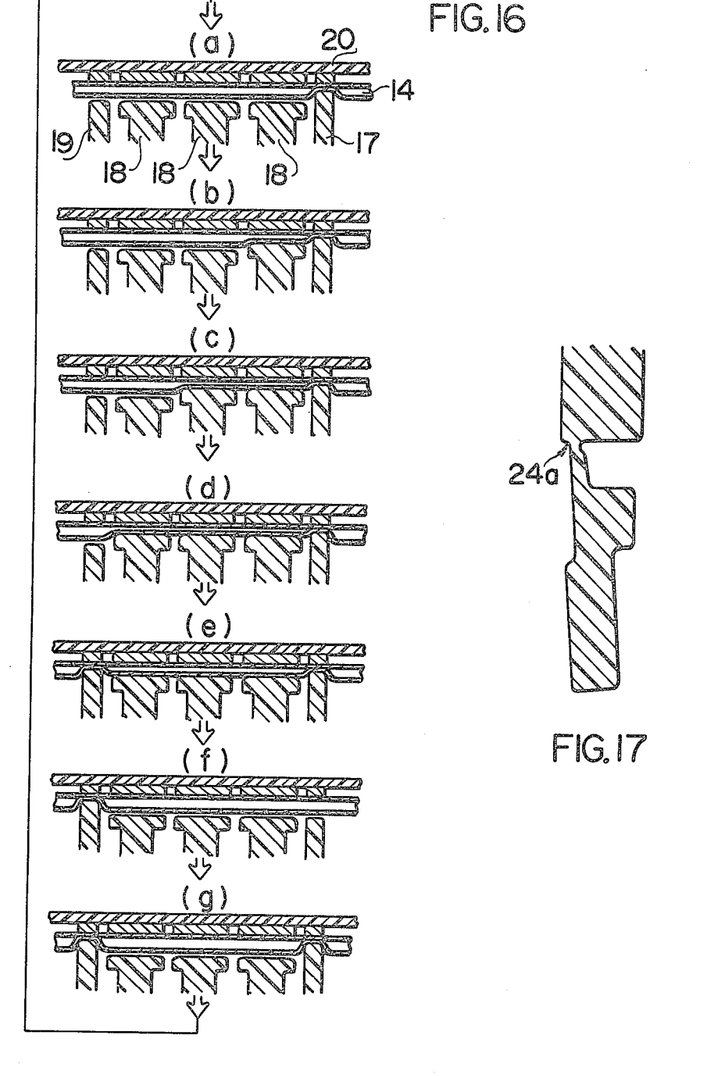
FIG. 16 shows modified sequential steps in the finger operation of five fingers.
FIG. 17 is a sectional view showing the fingers carried by the support frame at a folding zone of markedly reduced thickness according to a modification of the present invention.

(i) The fingers and the support means may be integrally molded or machined from crystalline plastic material such as polyacetal, polyethylene, polypropylene or polyamide, and the cantilevered end parts of the fingers may be folding parts 24a with the smallest possible thickness in the direction of the cap and cam. In this case, the camming operation results in finger movement about the folding parts as a center so that there is less driving power loss than when the plate spring portions are used. Also, the crystalline plastic material is durable and highly resistant to torsion and increases in strength with continued use because stress application in a constant direction results in an orderly rearrangement of the high polymer crystal lattice.

From the foregoing it is seen that the infusion device of the present invention comprises a finger-type pump unit in which a feeding tube is sandwiched between three or more fingers and the cap and squeezed thereby to dispense the medication, wherein both side fingers of lesser width and one, two or more inner or central fingers of greater width are supported by plate spring portions in cantilevered fashion, so that the fingers are peristaltically displaced by a cam formed as a unitary body with a common axis. Thus the number of components and manufacturing steps may be markedly reduced over the prior-art infusion device having the conventional pump unit. Moreover, the finger guides in the pump unit may be omitted to improve durability and cut power consumption by eliminating frictionally engaging parts.

According to a modification, when the support frame is divided into upper and lower frame sections encircling the fingers, cam assembly operation can be facilitated considerably. When the fingers and the support frame are molded integrally and the finger roots are reduced in thickness so as to be used as plate spring portions, the number of components in the device can be minimized and the dimensional and assembly precision improved to offset the higher costs entailed by metallic molds. If the fingers are oscillational by pins or connected by metallic plates to the support frame, then the metallic molds for the fingers and the frame can be simplified. Adjustment of the dispensed liquid dose is facilitated when the gap control sheet is affixed to the inner surface of the cap and flexed by the screw to provide an adjustable gap between it and the central finger. Finally, when mounting plates for rotary drive means such as motors are formed integrally with the support frame and the connecting portions are formed with slits, the number of components can be minimized with a facilitated assembly operation.

Thus it is seen that merely adopting a small size version of the conventional pump unit as in the prior art increases the number of components and gives rise to accumulated fitting and assembly errors that may affect the precision of the pump structure and, hence, of the infusion device containing the pump. In accordance with the present invention, however, pump fitting and assembly errors can be eliminated and the relative error ratio accompanying the reduction in size can be reduced to assure the desired pumping accuracy. The infusion device therefore exhibits improved infusion efficiency. In addition, the infusion device is durable because frictional pump components are eliminated. Owing to reduced power consumption, moreover, the battery lasts longer. This is an extremely important feature which makes the infusion device sufficiently portable.

As many apparently widely different embodiments of the present invention may be made without departing from the spirit and scope thereof, it is to be understood that the invention is not limited to the specific embodiments thereof except as defined in the appended claims.

What is claimed is:

1. In a device for infusion of liquid medication including a finger-type pump unit, said pump unit comprising a cap and at least three elongate fingers arranged to be displaceable towards said cap in a predetermined sequence, cam means for operating said fingers and rotary drive means for driving said cam means, said fingers being operative to squeeze a feeding tube for infusion of medication when said feeding tube is placed between said cap and said fingers, the improvement wherein said at least three fingers comprise two side fingers placed in generally parallel relation with and on both sides of at least one central finger, said side fingers each being constructed and arranged to squeeze said feeding tube at corresponding substantially point locations on said feeding tube for collapsing said tube substantially completely at said point locations, and said central finger being constructed and arranged to collapse said feeding tube over a required length between said point locations for pumping medication in the tube, a support member formed integrally at first ends of each of said fingers for supporting said fingers in cantilevered fashion, said support member being in the form of a support frame at least partially encircling the fingers in substantially the same plane as the fingers and said support member including an integrally formed mounting plate for mounting the rotary drive means, said fingers each having a reduced thickness portion at the first ends thereof in the direction toward said cap, and a plurality of cams forming said cam means wherein each cam has a specific cam profile and is operatively associated with a corresponding one of said fingers for operating the finger, said cams having a common axis which extends transversely of the axes of said fingers.

2. The device according to claim 1, wherein a control sheet of flexible material is placed directly on the surface of said cap facing said central finger, said sheet is secured to said cap at an end of said control sheet out of the region of said cap that confronts said feeding tube, so that a portion of said control sheet may be urged in the direction of said feeding tube to at least partially compress said feeding tube.

3. The device according to claim 2, comprising screw means on said cap for urging the control sheet in the direction of the feeding tube wherein said screw means presses said sheet from said cap.

4. The device according to claim 1, wherein the reduced thickness portion of each said finger is arranged as a plate spring portion.

5. The device as claimed in claim 1 wherein said fingers are made of crystalline plastic material.

6. The device according to the claim 5 wherein said crystalline plastic material is polyacetal.

7. The device according to claim 1, including mounting plate means for mounting the rotary drive means and formed integrally with the support frame, said mounting plate means having slits to afford said support frame with flexibilty relative to said mounting plate means when the rotary drive means is mounted on said mounting plate means.

8. The device according to claim 1, wherein said support frame comprises upper half frame sections which form outer boundaries over the lengths of said side fingers, said frame sections having slits on surfaces facing said cover, said slits being aligned transversely of the long axes of the fingers for accommodating said feeding tube in a stable state.

9. The device according to claim 1 wherein said cams are formed as a unitary body having a common axis, with the end cams having a maximum radius smaller than the minimum radius of the axially central portion of said body adjacent to said end cams.

* * * * *